United States Patent
Kesterson et al.

(10) Patent No.: US 9,404,848 B2
(45) Date of Patent: Aug. 2, 2016

(54) APPARATUSES AND METHODS FOR TESTING ADHESION OF A SEAL TO A SURFACE

(71) Applicant: The Boeing Company, Chicago, IL (US)

(72) Inventors: Matthew G. Kesterson, Everett, WA (US); Jane Shin, Seattle, WA (US); Roger A. Gage, Marysville, WA (US)

(73) Assignee: THE BOEING COMPANY, Chicago, IL (US)

( * ) Notice: Subject to any disclaimer, the term of this patent is extended or adjusted under 35 U.S.C. 154(b) by 136 days.

(21) Appl. No.: 14/205,258

(22) Filed: Mar. 11, 2014

(65) Prior Publication Data

US 2015/0260634 A1 Sep. 17, 2015

(51) Int. Cl.
*G01N 19/04* (2006.01)
*G01N 3/307* (2006.01)
*G01M 99/00* (2011.01)

(52) U.S. Cl.
CPC ............. *G01N 19/04* (2013.01); *G01M 99/007* (2013.01); *G01N 3/307* (2013.01)

(58) Field of Classification Search
CPC ............. G01N 19/04; G10L 1/02; G10L 1/08
USPC ........................................................ 73/150 A
See application file for complete search history.

(56) References Cited

U.S. PATENT DOCUMENTS

| | | | | |
|---|---|---|---|---|
| 2,625,585 A | * | 1/1953 | Krouse | G01B 7/105 324/202 |
| 3,282,094 A | * | 11/1966 | Hinden | G01N 3/42 73/150 R |
| 3,527,093 A | * | 9/1970 | Sellers | G01N 19/04 73/150 R |
| 3,543,065 A | * | 11/1970 | Phelan | G01N 29/2437 310/336 |
| 4,034,603 A | * | 7/1977 | Leeb | G01N 3/48 73/12.09 |
| 4,104,603 A | * | 8/1978 | Wheeler | H01H 5/02 335/207 |
| 4,392,305 A | * | 7/1983 | Nix | G01B 7/105 324/230 |
| 4,470,293 A | * | 9/1984 | Redmon | G01N 3/307 73/12.09 |
| 4,586,371 A | * | 5/1986 | Ivie | G01N 19/04 73/150 A |
| 4,776,202 A | * | 10/1988 | Brar | G01N 3/303 73/12.13 |
| 4,821,578 A | * | 4/1989 | Brar | G01N 3/303 73/827 |
| 4,884,175 A | * | 11/1989 | Weng | G01L 17/00 362/116 |

(Continued)

OTHER PUBLICATIONS

Pink Pearl Eraser, manufactured by Paper Mate, 1 page, published at least as early as Mar. 10, 2013.

(Continued)

*Primary Examiner* — Lisa Caputo
*Assistant Examiner* — Tran M Tran

(57) ABSTRACT

One example of the disclosure relates to an apparatus for testing adhesion of a seal to a surface. The apparatus includes a first member and a second member movable relative to the first member. The second member includes a seal-contact member. The apparatus also includes means for biasing the first member and the second member relative to each other with a biasing force and an indicator on one of the first member or the second member.

20 Claims, 10 Drawing Sheets

(56) References Cited

U.S. PATENT DOCUMENTS

| | | | | |
|---|---|---|---|---|
| 4,896,543 | A * | 1/1990 | Gullman | B43K 8/22 382/314 |
| 5,006,799 | A * | 4/1991 | Pfanstiehl | G01B 7/105 324/230 |
| 5,176,026 | A * | 1/1993 | Leeb | G01N 3/52 73/79 |
| 5,257,088 | A * | 10/1993 | Tyson, II | G01B 11/161 244/125 |
| 5,290,972 | A * | 3/1994 | Someya | G06F 3/03545 178/19.04 |
| 5,649,447 | A * | 7/1997 | Van Avery | G01N 19/04 73/150 A |
| 5,666,715 | A * | 9/1997 | Zoiss | B25D 11/064 173/117 |
| 5,679,904 | A * | 10/1997 | Stets | G01N 19/04 73/46 |
| 6,050,140 | A * | 4/2000 | Koch | A01N 19/04 73/150 A |
| 6,056,283 | A * | 5/2000 | Gage | B25B 31/005 269/48.4 |
| 6,393,905 | B1 * | 5/2002 | Steele | G01N 19/04 73/150 R |
| 6,513,374 | B2 * | 2/2003 | Goh | H01L 21/67132 73/150 A |
| 6,557,426 | B2 * | 5/2003 | Reinemann, Jr. | G10L 5/0033 73/862.393 |
| 6,718,647 | B2 * | 4/2004 | Trull | G01B 5/012 33/558 |
| 7,265,750 | B2 * | 9/2007 | Rosenberg | A63F 13/06 178/18.04 |
| 7,266,878 | B1 * | 9/2007 | Sullivan | H01R 43/015 29/33 M |
| 7,475,475 | B2 * | 1/2009 | Sullivan | H01R 43/015 29/566.4 |
| 7,511,705 | B2 * | 3/2009 | Silk | G06F 1/3203 345/179 |
| 7,523,672 | B2 * | 4/2009 | Lapstun | B43K 7/005 73/818 |
| 7,528,825 | B2 * | 5/2009 | Sakurai | G06F 3/03545 345/156 |
| 7,657,128 | B2 * | 2/2010 | Silverbrook | B41J 2/17503 382/312 |
| 7,765,853 | B2 * | 8/2010 | Safai | G01M 3/363 73/40 |
| 7,891,253 | B2 * | 2/2011 | Shipton | G01D 5/3473 73/780 |
| 7,898,532 | B2 * | 3/2011 | Lapstun | B43K 7/005 178/19.01 |
| 7,928,967 | B2 * | 4/2011 | Underwood | B43K 7/005 345/179 |
| 7,955,017 | B2 * | 6/2011 | Lapstun | B43K 7/005 345/179 |
| 7,969,587 | B2 * | 6/2011 | Silverbrook | B41K 2/17503 345/156 |
| 7,974,500 | B2 * | 7/2011 | Silverbrook | B41J 2/17503 382/313 |
| 8,091,440 | B2 * | 1/2012 | Kim | G01M 3/04 211/190 |
| 8,261,620 | B2 * | 9/2012 | Brandestini | G01N 3/307 73/803 |
| 8,308,387 | B2 * | 11/2012 | King | G02B 26/06 345/179 |
| 8,414,210 | B2 * | 4/2013 | Silverbrook | G06F 3/0317 347/179 |
| 8,593,437 | B2 * | 11/2013 | Liang | B43K 24/14 345/179 |
| 8,604,801 | B2 * | 12/2013 | Tarone | G01R 31/045 324/538 |
| 8,619,064 | B2 * | 12/2013 | Knee | G06F 3/016 178/19.04 |
| 8,688,186 | B1 * | 4/2014 | Mao | A61B 5/1455 600/202 |
| 8,723,842 | B2 * | 5/2014 | Kaneda | G06F 3/03545 178/18.07 |
| 8,749,533 | B2 * | 6/2014 | Adhikari | G06F 3/016 345/156 |
| 8,773,403 | B2 * | 7/2014 | Adhikari | G06F 3/0354 178/19.01 |
| 8,978,487 | B2 * | 3/2015 | Fergusson | G06F 3/03545 345/179 |
| 9,095,947 | B1 * | 8/2015 | DeLand | B23Q 17/099 |
| 2002/0158854 | A1 * | 10/2002 | Ju | G06F 3/03545 345/179 |
| 2003/0037604 | A1 * | 2/2003 | Poblete | G01M 3/32 73/73 |
| 2003/0146906 | A1 * | 8/2003 | Lin | G06F 3/03545 345/179 |
| 2005/0248549 | A1 * | 11/2005 | Dietz | G06F 3/016 345/179 |
| 2005/0271458 | A1 * | 12/2005 | Kui | B43K 29/08 401/195 |
| 2011/0102379 | A1 * | 5/2011 | Lapstun | B43K 7/005 345/179 |

OTHER PUBLICATIONS

Frixion Eraser, manufactured by Pilot Corporation, 1 page, published at least as early as Mar. 10, 2013.

* cited by examiner

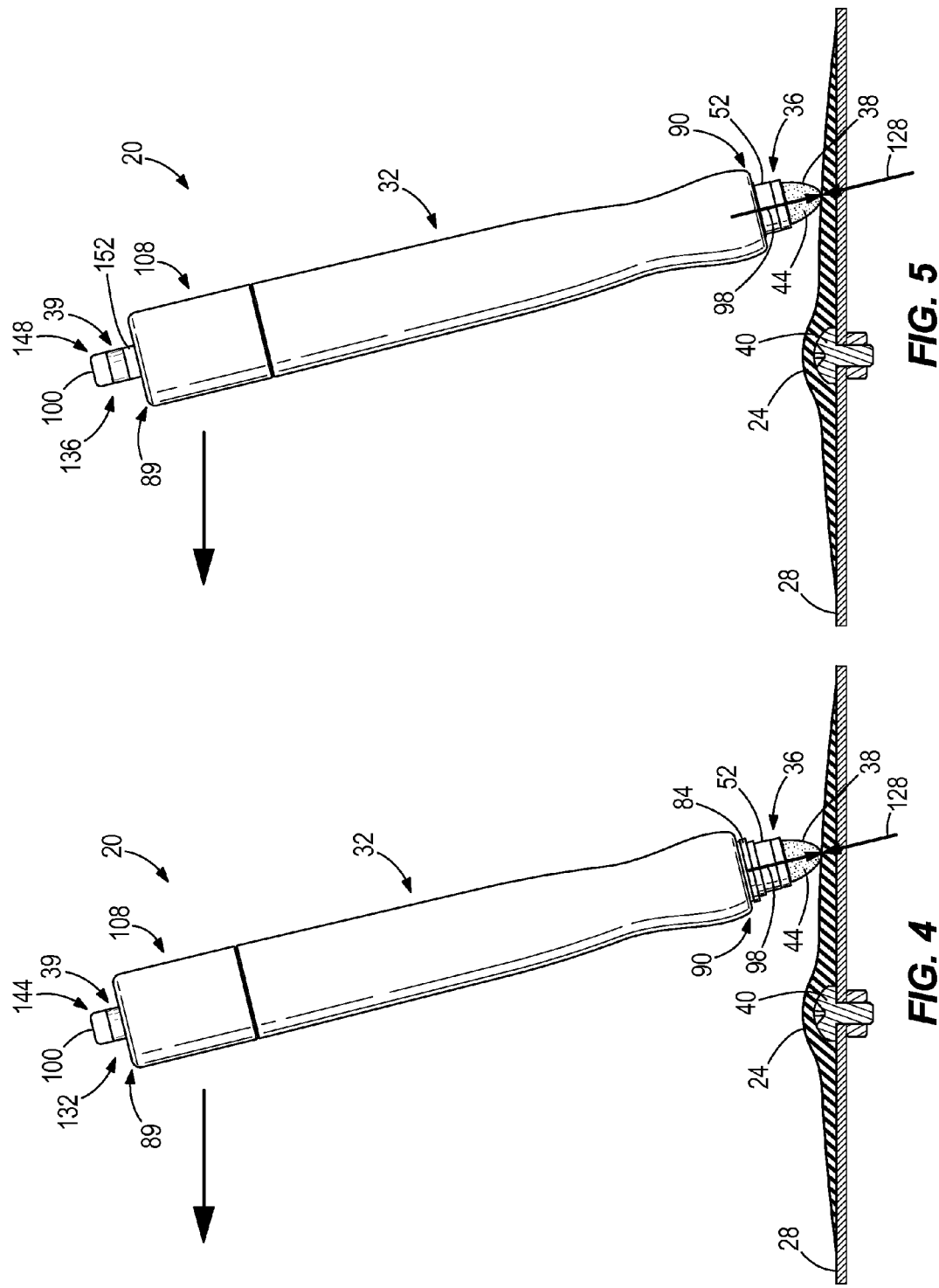

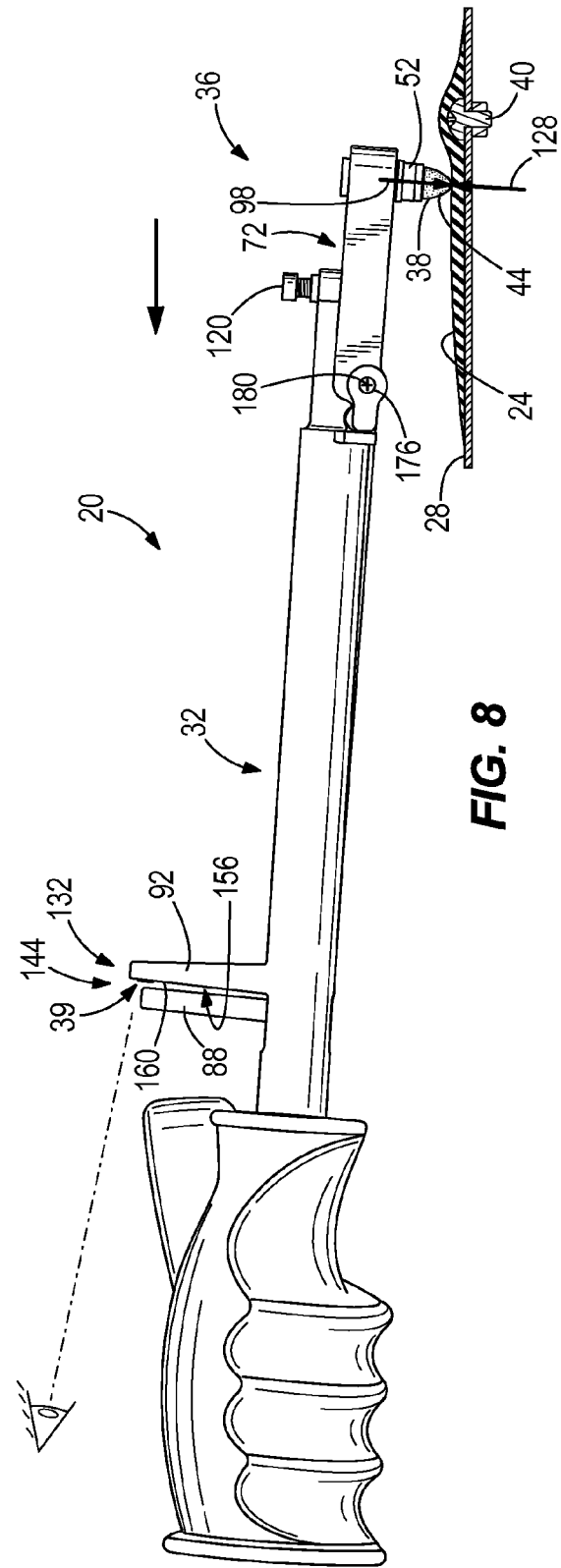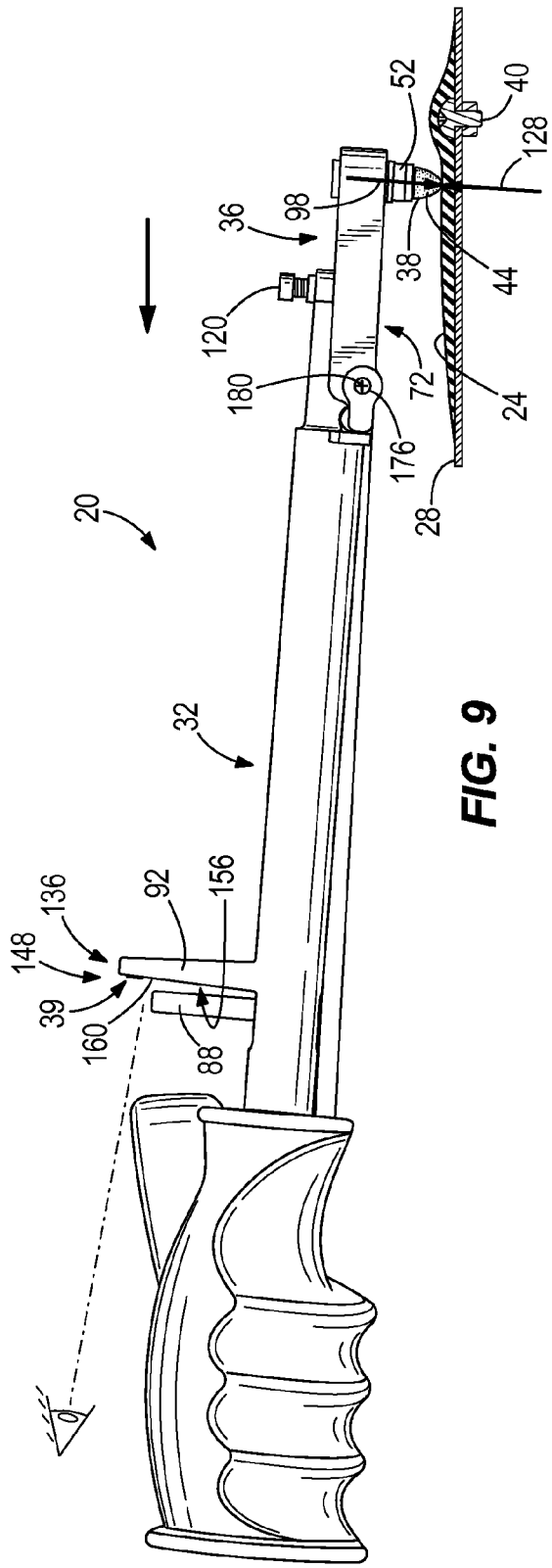

APPARATUSES AND METHODS FOR TESTING ADHESION OF A SEAL TO A SURFACE

BACKGROUND

During manufacture of assemblies, it is often necessary to seal portions of associated fasteners and/or joints between various surfaces. Seals are commonly tested to ensure adequate seal adhesion. Known methods of testing adhesion of seals to surfaces include a subjective component and may therefore yield inconsistent results not only between different operators, but also from one operation to another.

SUMMARY

Accordingly, apparatuses and methods for testing adhesion of a seal to a surface, intended to address the above-identified concerns, would find utility.

One example of the present disclosure relates to an apparatus for testing adhesion of a seal to a surface. The apparatus includes a first member and a second member movable relative to the first member. The second member includes a seal-contact member. The apparatus also includes means for biasing the first member and the second member relative to each other with a biasing force and an indicator on one of the first member or the second member.

One example of the present disclosure relates to a method of testing adhesion of a seal to a surface. The method includes applying a force to the seal and indicating an amount of the force applied to the seal.

BRIEF DESCRIPTION OF THE DRAWINGS

Figure 1:
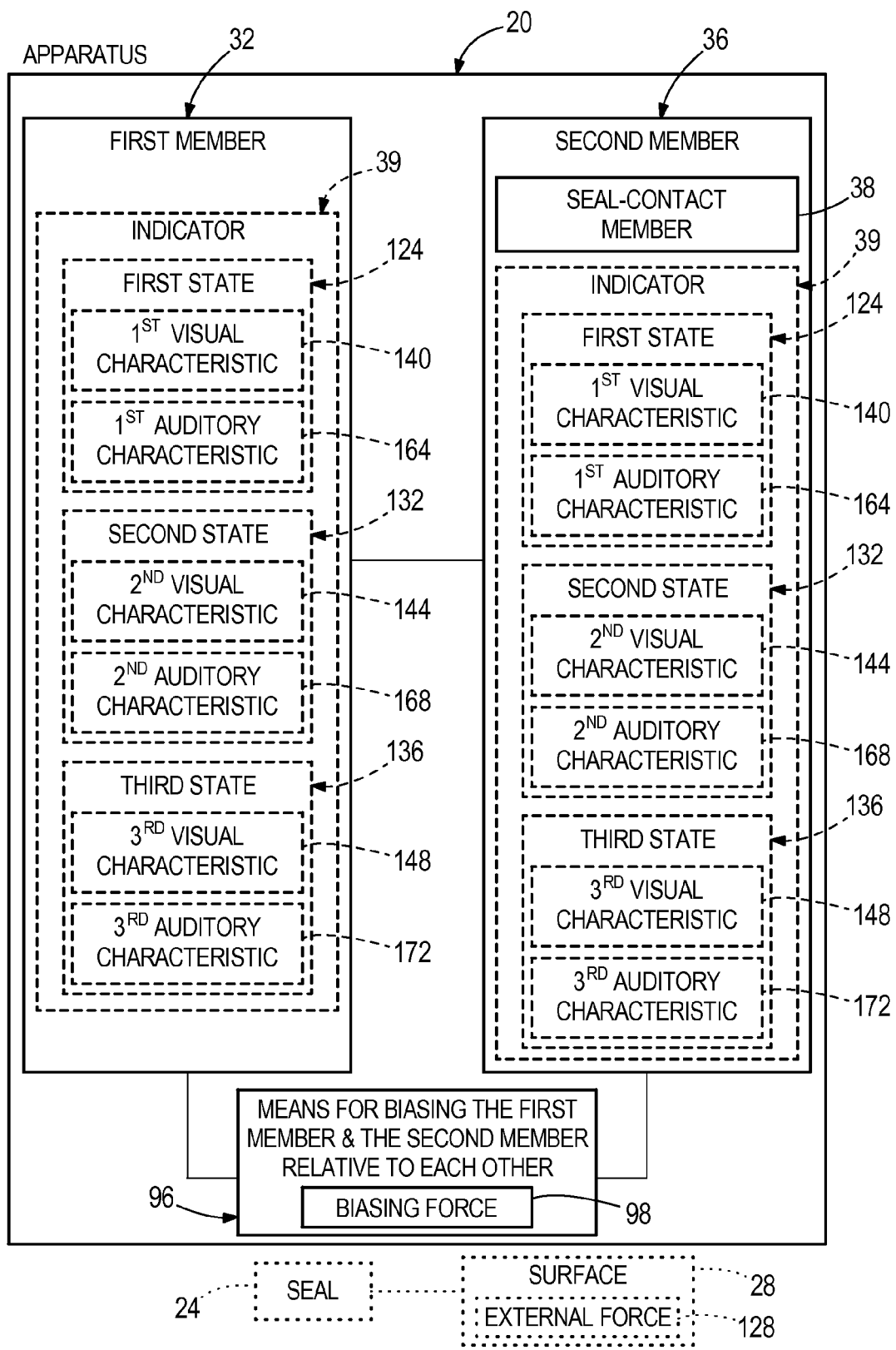
Figure 2:
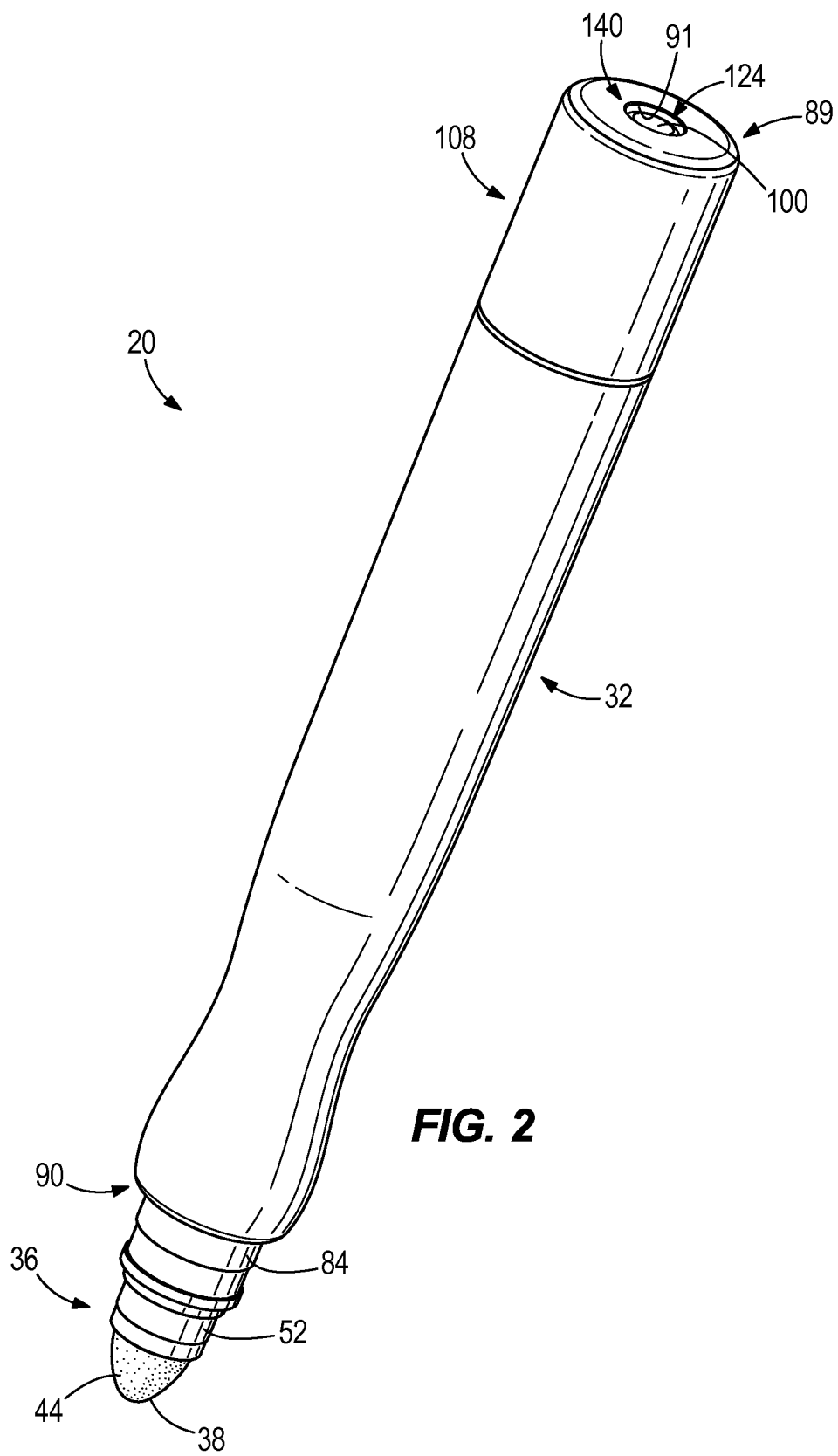
Figure 3:
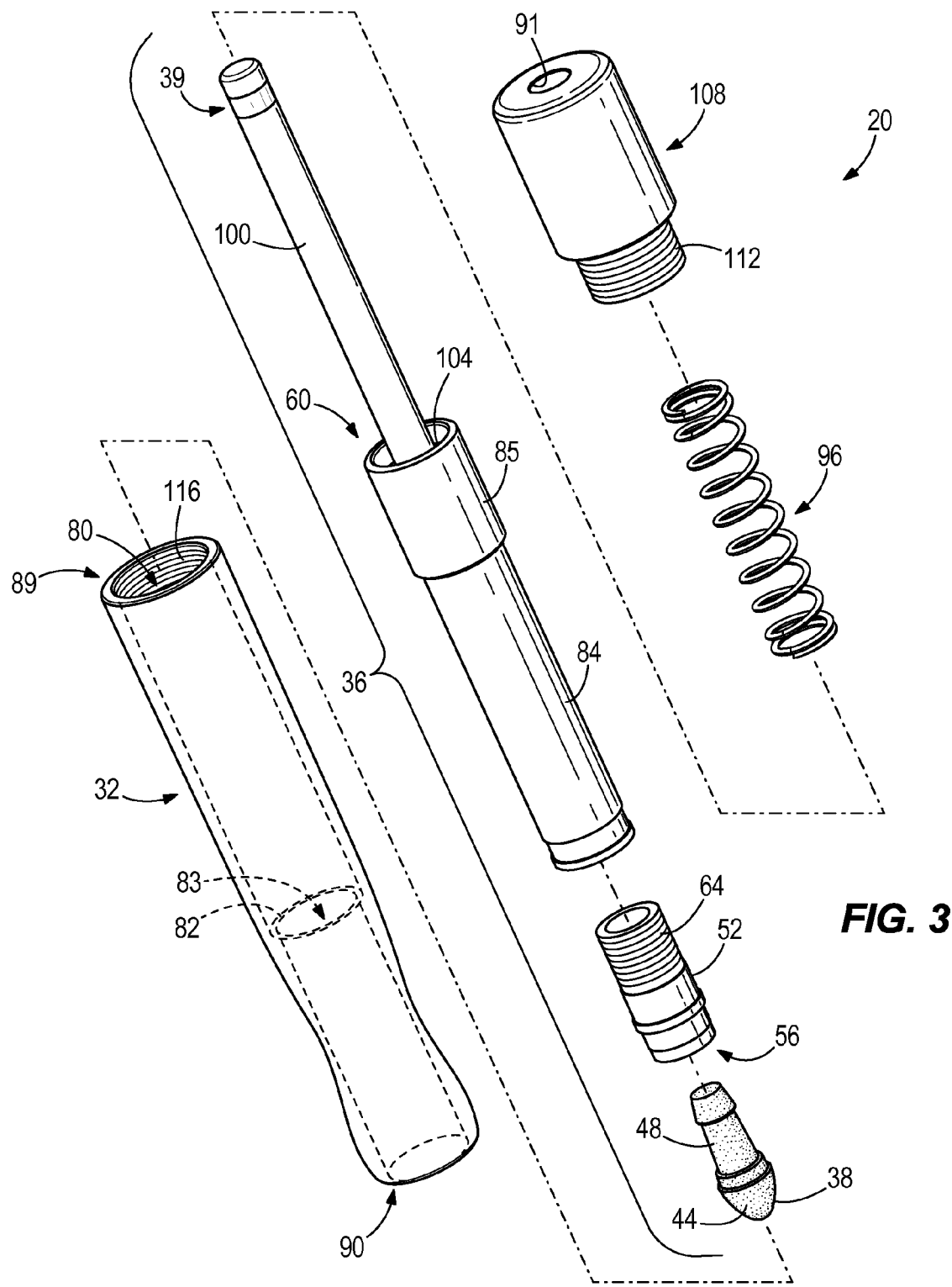
Figure 6:
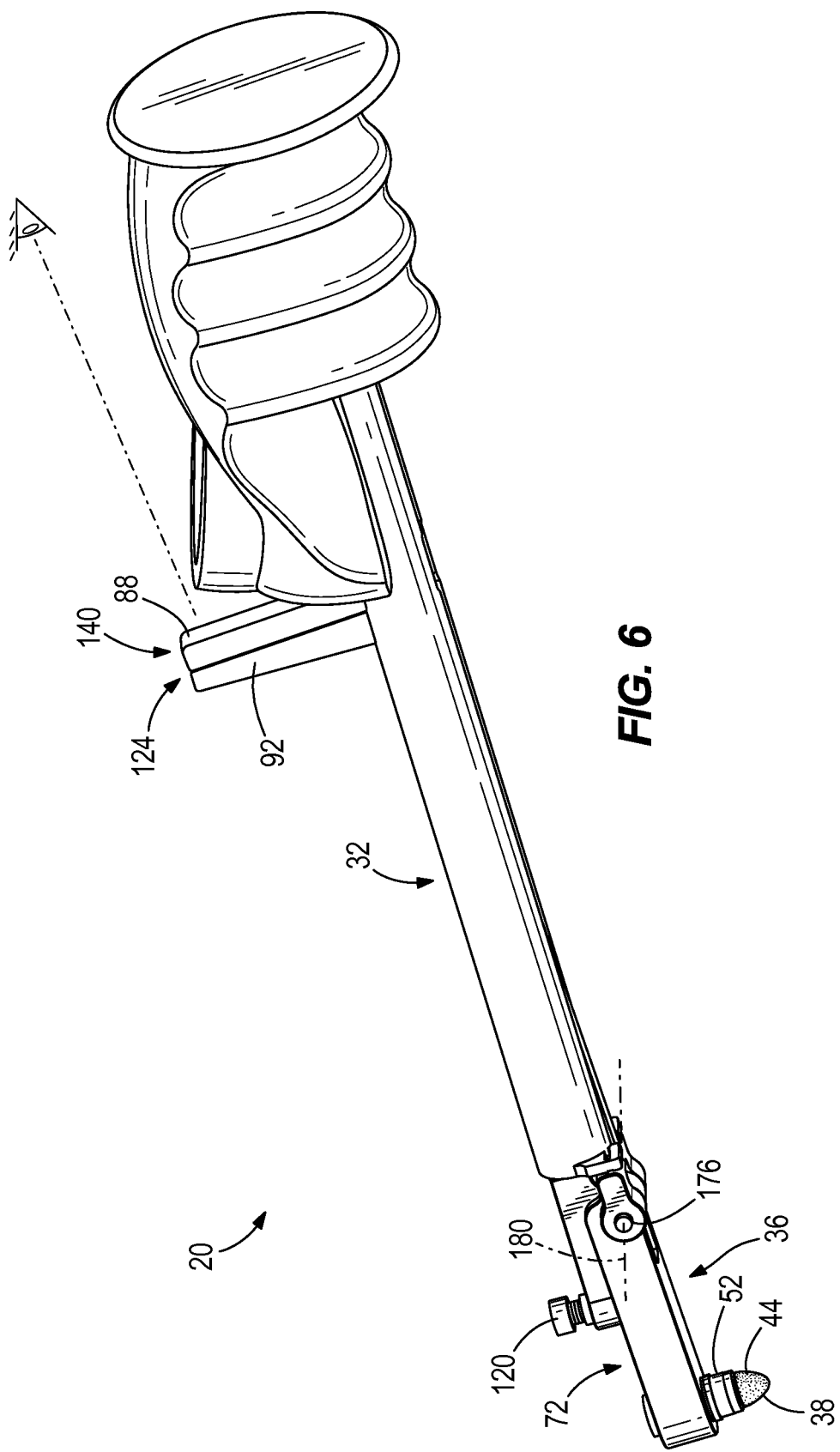
Figure 7:
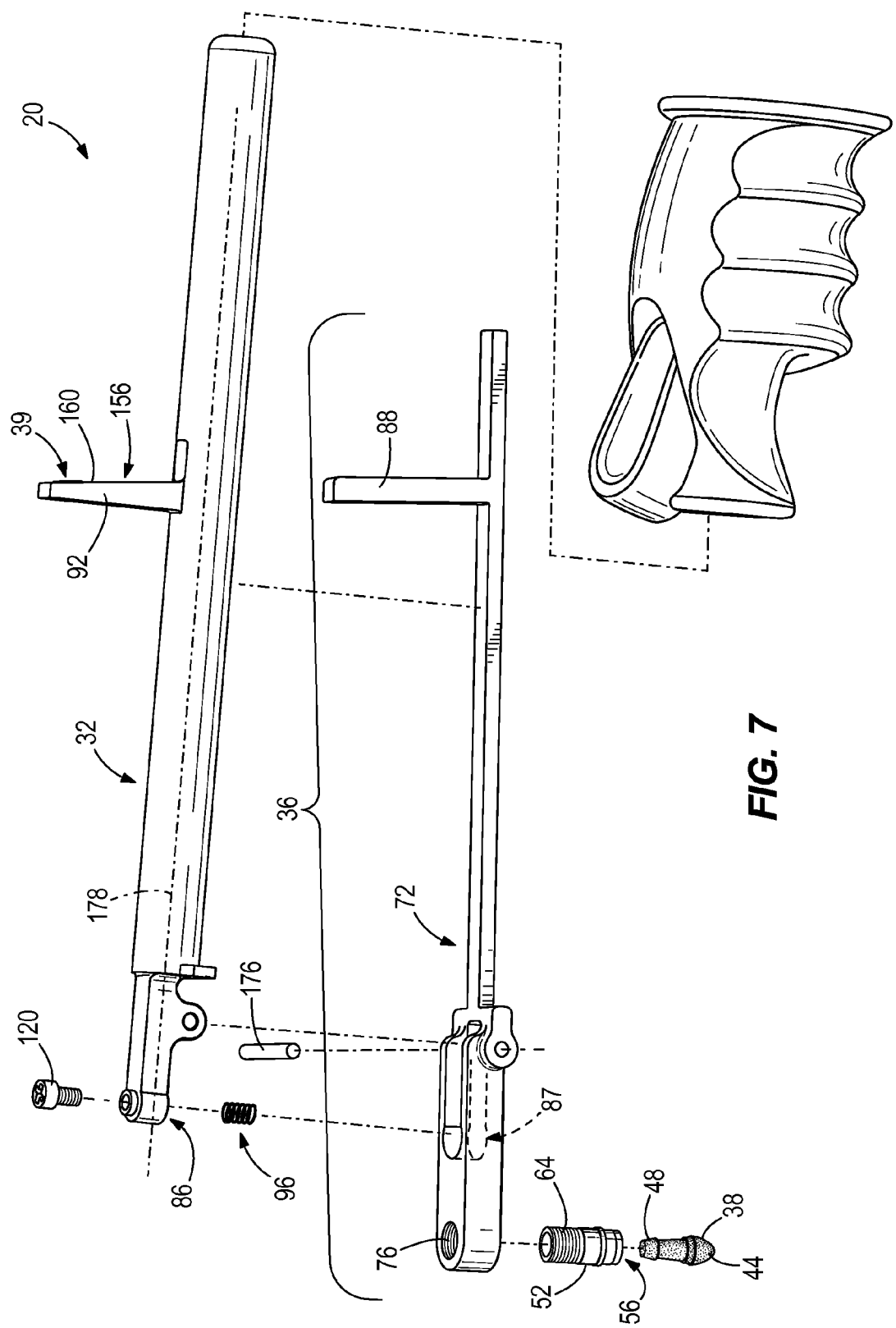
Figure 10:
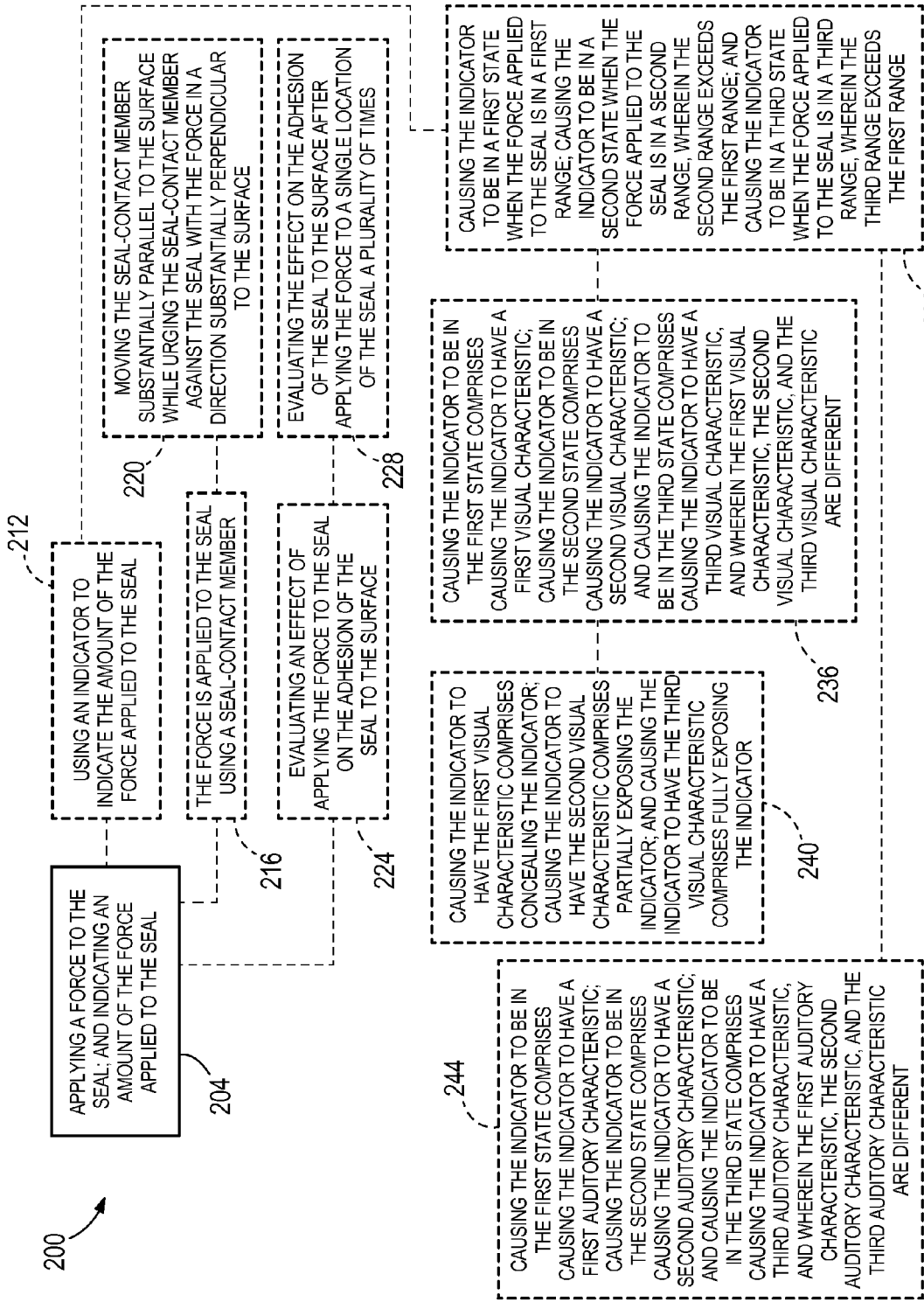
Figure 11:
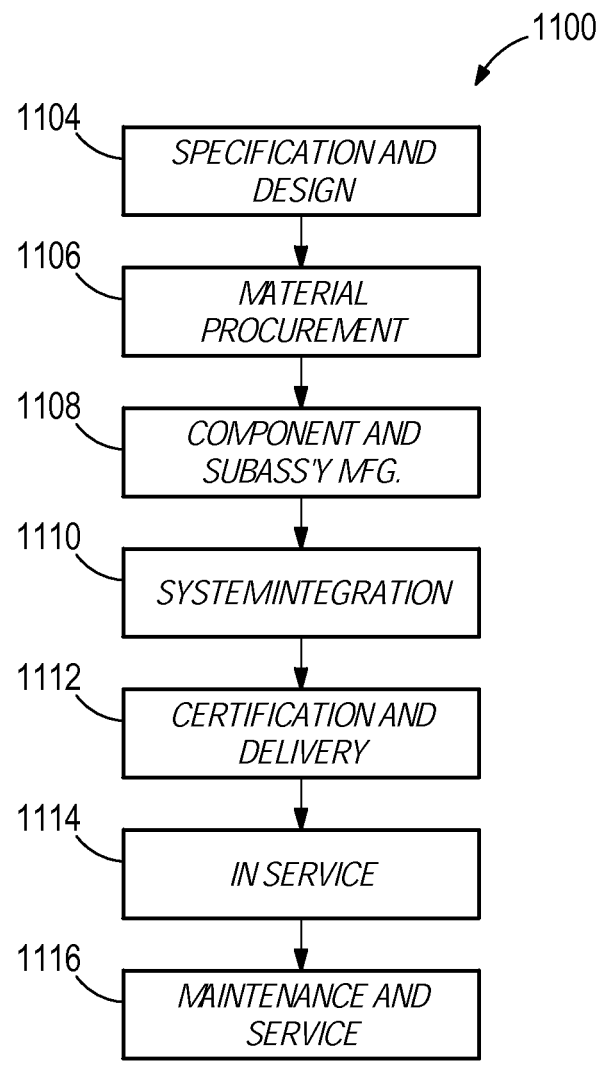
Figure 12:
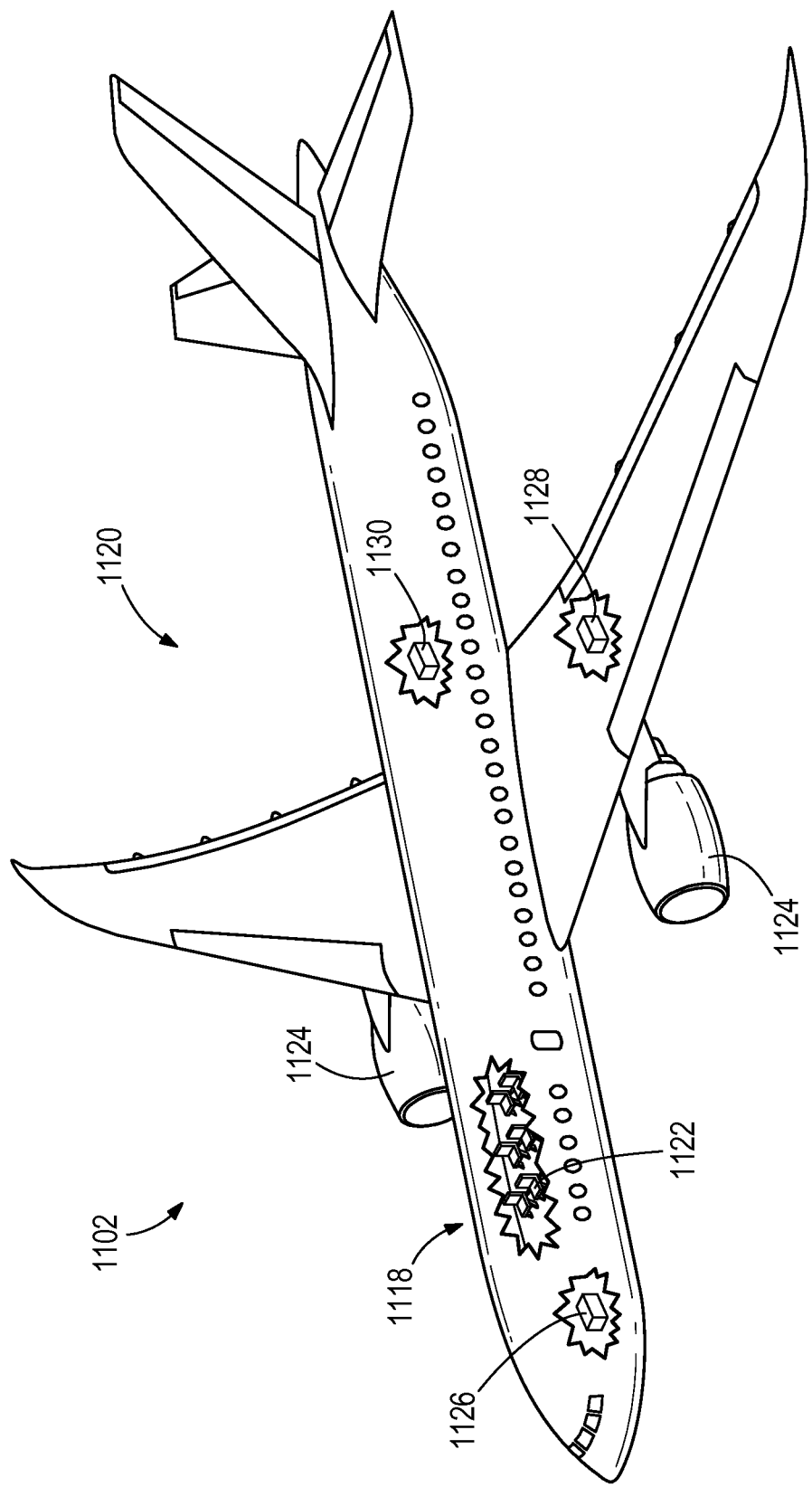

Having thus described examples of the disclosure in general terms, reference will now be made to the accompanying drawings, which are not necessarily drawn to scale, and wherein like reference characters designate the same or similar parts throughout the several views, and wherein:

FIG. 1 is a block diagram of an apparatus for testing adhesion of a seal to a surface, according to one aspect of the present disclosure;

FIG. 2 is a schematic top perspective view of the apparatus of FIG. 1, according to one aspect of the present disclosure;

FIG. 3 is a schematic exploded perspective view of the apparatus shown in FIG. 2, according to one aspect of the present disclosure;

FIG. 4 is a schematic side elevation view of the apparatus shown in FIG. 2 engaging a seal adhered to a surface, according to one aspect of the present disclosure;

FIG. 5 is a schematic side elevation view of the apparatus shown in FIG. 2 engaging a seal adhered to a surface, according to one aspect of the present disclosure;

FIG. 6 is a schematic perspective view of the apparatus of FIG. 1, according to one aspect of the present disclosure;

FIG. 7 is a schematic exploded perspective view of the apparatus shown in FIG. 6, according to one aspect of the present disclosure;

FIG. 8 is a schematic side elevation view of the apparatus shown in FIG. 6 engaging a seal adhered to a surface, according to one aspect of the present disclosure;

FIG. 9 is a schematic side elevation view of the apparatus shown in FIG. 6 engaging a seal adhered to a surface, according to one aspect of the present disclosure;

FIG. 10 is a flow diagram of a method of testing adhesion of a seal to a surface, according to one aspect of the present disclosure;

FIG. 11 is a flow diagram of aircraft production and service methodology, according to one aspect of the present disclosure; and FIG. 12 is a schematic perspective view of an aircraft, according to one aspect of the present disclosure.

In the block diagram(s) referred to above, solid lines connecting various elements and/or components may represent mechanical, electrical, fluid, optical, electromagnetic and other couplings and/or combinations thereof. As used herein, "coupled" means associated directly as well as indirectly. For example, a member A may be directly associated with a member B, or may be indirectly associated therewith, e.g., via another member C. Couplings other than those depicted in the block diagram(s) may also exist. Dashed lines, if any, connecting the various elements and/or components represent couplings similar in function and purpose to those represented by solid lines; however, couplings represented by the dashed lines are either selectively provided or relate to alternative or optional aspects of the disclosure. Likewise, any elements and/or components, represented with dashed lines, indicate alternative or optional aspects of the disclosure. Environmental elements, if any, are represented with dotted lines.

In the flow diagram(s) referred to above, the blocks may represent operations and/or portions thereof. Moreover, lines connecting the various blocks do not imply any particular order of or dependency between the operations or portions thereof.

DETAILED DESCRIPTION

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Reference herein to "one example" or "one aspect" means that one or more feature, structure, or characteristic described in connection with the example or aspect is included in at least one implementation. The phrase "one example" or "one aspect" in various places in the specification may or may not be referring to the same example or aspect.

Referring generally to FIGS. 1-9 and in particular to FIG. 1, one example of the present disclosure relates to an apparatus 20 for testing adhesion of a seal 24 to a surface 28. The apparatus 20 includes a first member 32 and a second member 36, movable relative to the first member 32. The second member 36 includes a seal-contact member 38. The apparatus 20 also includes means 96 for biasing the first member 32 and the second member 36 relative to each other with a biasing force 98 and an indicator 39 on one of the first member 32 or the second member 36. As used herein, "to bias" is to apply a steady force.

Referring, e.g., to FIGS. 4, 5, 8 and 9, the seal 24 may be any of a wide variety of sealants or adhesives, flowable in the uncured state for application to a surface 28 e.g., with a dispenser (not shown), and then cured to pliable, semi-hard, or hard condition. The surface 28 may be one of different surfaces in a variety of environments, such as an assembly of an aircraft 1102 (see, e.g., FIG. 12) and a fastener 40 may be used to couple parts of such an assembly together. The seal 24 may be applied and adhered to at least a portion of the fastener 40 and/or at least a portion of at least one surface, such as the surface 28.

Referring generally to FIGS. 1-9, and particularly to FIGS. 3 and 7, in one aspect of the disclosure, which may include at least a portion of the subject matter of any of the preceding and/or following examples and aspects, the seal-contact member 38 is an elastic member. The seal-contact member 38 may include a nose portion 44, engageable with the seal 24, and a coupling portion 48 for mating with a coupling member 52. The coupling portion 48 of the seal-contact member 38 may be removably retained within a cavity 56 defined in the coupling member 52 via, e.g., an interference fit or a snap-fit. The seal-contact member 38 may be removed from the coupling member 52 and a replacement seal-contact member 38 may be coupled to the coupling member 52 when the original seal-contact member 38 becomes worn, damaged, or when it is otherwise desirable to replace the seal-contact member 38.

Referring generally to, e.g., FIGS. 3-5 and particularly to FIG. 3, in one example, the second member 36 may include a plunger 60. The coupling member 52 may be attached to the plunger 60 and moveable with the plunger 60 relative to the first member 32. In one example, the coupling member 52 is threaded into the plunger 60. The coupling member 52 includes external threads 64 defined in an outer surface thereof and the plunger 60 includes internal threads (not shown) defined in a cavity in the plunger 60. The external threads 64 and internal threads are complementary to provide a threaded joint between the coupling member 52 and the plunger 60. In other examples, the coupling member 52 may be attached to the plunger 60 by other means, such as mechanical fastening, interference joining, bonding, or welding. Alternatively, the plunger 60 and the coupling member 52 may be formed as a unitary structure.

Referring, e.g., to FIGS. 6-9, in one example, the second member 36 may include an elongated arm 72. The coupling member 52 may be coupled to and moveable with the arm 72. In one example, the coupling member 52 may be attached at one end of the arm 72. The coupling member 52 may include external threads 64 defined in an outer surface thereof and the arm 72 may include internal threads 76 defined in a cavity formed, e.g., proximate one end of the arm 72. The external threads 64 and internal threads 76 are complementary to provide a threaded joint between the coupling member 52 and the arm 72. In other examples, the coupling member 52 may be attached to the arm 72 by other means, such as mechanical fastening, interference joining, bonding, or welding. Alternatively, the arm 72 and the coupling member 52 may be formed as a unitary structure.

Referring, e.g., to FIGS. 1, 3, and 7, the means 96 may include a biasing member such as a coil spring. Alternatively, instead of or in addition to the coil spring, the means 96 may include a spring washer; a leaf spring; a conical or undulating washer, such as a Belleville washer; other resilient and/or elastic members such as, for example, a rubber member or a plastic member; a gas spring; a magnetic repulsion arrangement; an active or powered element such as, for example, a pneumatic device, a hydraulic device, an electrically powered device, a solenoid device, electromagnetic device, other device with pressurized fluid, or other electrically powered device; a finger; lever; gear; wedge; or the like.

As illustrated, e.g., in FIGS. 2-5, the means 96 is positioned around a portion 100 of the plunger 60 and is compressed between a shoulder 104 of the plunger 60 and a cap 108. The cap 108 is coupled to an end 89 of the first member 32 opposite an end 90 of the first member 32 from which the seal-contact member 38 projects. In one example, as shown in FIG. 3, the cap 108 is threaded to the first member 32. In this example, the cap 108 includes external threads 112 and the first member 32 includes internal threads 116 complementary to the external threads 112 to ensure threadable coupling between the cap 108 and the first member 32. The cap 108 may be coupled to the first member 32 in a variety of other ways including, but not limited to interference joining, bonding, welding, mechanical fastening, or the like. In one example, the first member 32 includes the cap 108 and the end 89 of the first member 32 is an end of the cap 108 opposite the end 90.

Referring, e.g., to FIGS. 3-5, in one aspect of the disclosure, which may include at least a portion of the subject matter of any of the preceding and/or following examples and aspects, the second member 36 is linearly movable relative to the first member 32. The second member 36 moves linearly relative to the first member 32 at least partially within a cavity 80 defined in the first member 32. Referring, e.g., to FIGS. 6-9, in one aspect of the disclosure, which may include at least a portion of the subject matter of any of the preceding and/or following examples and aspects, the second member 36 is angularly movable relative to the first member 32 and not linearly movable relative to the first member 32. The second member 36 is rotatable relative to the first member 32 about a pin 176. The pin 176 allows the second member 36 to angularly move relative to the first member 32 and prevents the second member 36 from linearly moving relative to the first member 32. The means 96 is compressed between the first member 32 and the second member 36. In this example, the means 96 is a coil spring and a fastener 120 is threaded into the first member 32 to insert into and retain the coil spring 96.

Referring generally to FIGS. 2-9, in one aspect of the disclosure, which may include at least a portion of the subject matter of any of the preceding and/or following examples and aspects, the second member 36 has a limited range of motion relative to the first member 32. As illustrated, e.g., in FIG. 3, in one example, the first member 32 defines the cavity 80, in which the second member 36 translates relative to the first member 32. The first member 32 includes a lip 82, defining a narrow cavity portion 83. The narrow cavity portion 83 is wider than a portion 84 of the plunger 60 to allow at least a portion of the second member 36 to project outwardly from the first member 32, but narrower than a portion 85 of the plunger 60. The means 96 applies the biasing force 98 to the plunger 60 to bias the plunger 60 in a first direction. In one example, the first direction is generally toward the end 90 (e.g., see FIG. 3) of the first member 32. The portion 85 is larger than the portion 84 to ensure that the portion 85 abuts the lip 82 and prevents further movement of the second member 36 relative to the first member 32 in the first direction. Movement of the second member 36 may also be limited relative to the first member 32 in a second direction, opposite the first direction. In one example, the second direction is generally toward the end 89 (e.g., see FIG. 3) of the first member 32. The seal-contact member 38 may be applied against the seal 24 (e.g., FIG. 4), which results in an external force 128 being applied to the second member 36 to cause the second member 36 to translate relative to the first member 32 in the second direction. The means 96 is compressed between the shoulder 104 of the plunger 60 and the cap 108 as the second member 36 moves in the second direction relative to the first member 32. The cap 108 is coupled to the end 89 of the first member 32 and defines an opening 91 therein. The opening 91 is narrower than the portion 85 of the plunger 60, but is wider than a portion 100 of the plunger 60 to allow the portion 100 to project outwardly of the cap 108 as the second member 36 moves in the second direction relative to the first member 32. The shoulder 104 of the portion 85 abuts the cap 108 if the second member 36 moves sufficiently far in the second direction relative to the first member 32. Abutment between the shoulder 104 and the cap 108 limits movement of the second member 36 relative to the first member 32 in the second direction.

As illustrated in FIGS. 6-9, in one example, the second member 36 has the arm 72, which includes an arm projection 88, and the first member 32 includes a first-member projection 92. In one example, the means 96 is compressed between a portion 86 of the first member 32 and a portion 87 of the second member 36. The means 96 biases the first member 32 and the second member 36 in a first angular direction relative to each other about the pin 176. Movement of the second member 36 relative to the first member 32 is limited in the first angular direction when the arm projection 88 engages the first-arm projection 92 (see, e.g., FIG. 6). The seal-contact member 38 may be applied against the seal 24 (e.g., FIG. 8), which results in the external force 128 being applied to the second member 36 to cause the arm 72 to rotate about the pin 176 relative to the first member 32 in a second angular direction opposite the first angular direction. The means 96 is compressed between the portion 86 of the first member 32 and the portion 87 of the second member 36 as the arm 72 of the second member 36 rotates in the second angular direction relative to the first member 32. Movement of the second member 36 in the second angular direction relative to the first member 32 is limited when the portion 86 of the first member 32 engages the portion 87 of the second member 36. Alternatively, movement of the second member 36 relative to the first member 32 in the first angular direction and the second angular direction may be limited in other ways.

Referring, e.g., to FIGS. 6-9, in one aspect of the disclosure, which may include at least a portion of the subject matter of any of the preceding and/or following examples and aspects, the first member 32 longitudinally extends along a direction 178 and the second member 36 is angularly movable relative to the first member 32 about an axis 180 perpendicular to the direction 178 and passing through the first member 32. With reference, e.g., to FIG. 6, the axis 180 is aligned with and a longitudinal axis of the pin 176.

Referring, e.g., to FIGS. 2-5, in one aspect of the disclosure, which may include at least a portion of the subject matter of any of the preceding and/or following examples and aspects, the second member 36 is at least partially enclosed by the first member 32. Referring to FIGS. 3-5, in one example, a part of the portion 100 of the plunger 60 protrudes from the end 89 of the first member 32 and a part of the coupling member 52 and the seal-contact member 38 protrude from the end 90 of the first member 32 when the external force 128 is applied to the seal-contact member 38, while the rest of the second member 36 is contained within the first member 32. Referring to FIG. 2, in one example, a part of the coupling member 52 and a part of the seal contact member 38 protrude from the end 90 of the first member 32 when no external force 128 is applied to the seal contact member 38, while the remainder of second member 36 is contained within the first member 32.

Referring generally to FIGS. 1-9, in one aspect of the disclosure, which may include at least a portion of the subject matter of any of the preceding and/or following examples and aspects, the indicator 39 is in a first state 124 when the external force 128 applied to the second member 36 in a direction opposite to the biasing force 98 is in a first force range (see, e.g., FIGS. 2 and 6). The indicator 39 is in a second state 132 when the external force 128 is in a second force range (see, e.g., FIGS. 4 and 8) that exceeds the first force range. Furthermore, the indicator 39 is in a third state 136 when the external force 128 is in a third force range (see, e.g., FIGS. 5 and 9) that exceeds the second force range. When the external force 128 is in the first force range, the biasing force 98 may be considered insufficient for the purposes of testing the adhesion of the seal 24 to the surface 28. When the external force 128 is in the second force range, the biasing force 98 may be considered adequate. When the external force 128 is in the third force range, the biasing force 98 may be considered excessive. The indicator 39 may have a number of states different from or in addition to the first state 124, the second state 132, and the third state 136 to indicate the magnitude of the biasing force 98 applied to the seal 24 responsive to the external force 128. Those skilled in the art will appreciate that the external force 128 is equal in magnitude and opposite in direction to a force applied to the second member 32 by a human operator or a robotic end effector.

Referring generally to FIGS. 1-9, in one aspect of the disclosure, which may include at least a portion of the subject matter of any of the preceding and/or following examples and aspects, the indicator 39 has a first visual characteristic 140 in the first state 124 (see, e.g., FIGS. 2 and 6), a second visual characteristic 144 in the second state 132 (see, e.g., FIGS. 4 and 8), and a third visual characteristic 148 in the third state 136 (see, e.g., FIGS. 5 and 9). As illustrated in FIGS. 2, 4-6, 8, and 9, the first visual characteristic 140, the second visual characteristic 144, and the third visual characteristic 148 are different, e.g., with respect to the visual perception of the indicator 39 by an observer utilizing the apparatus 20.

Referring generally to FIGS. 1-9, in one aspect of the disclosure, which may include at least a portion of the subject matter of any of the preceding and/or following examples and aspects, the indicator 39 is not observable in the first state 124 (see, e.g., FIGS. 2 and 6), is partially observable in the second state 132 (see, e.g., FIGS. 4 and 8), and is fully observable in the third state 136 (see, e.g., FIGS. 5 and 9).

As illustrated in FIG. 2, in one example, when the magnitude of the external force 128 is below a specific threshold, the indicator 39 is in the first state 124 and is fully enclosed within the first member 32, so that it is not observable. As illustrated in FIG. 4, in one example, when the magnitude of the external force 128 is increased to a specific range, the indicator 39 is in the second state 132 and partially projects outwardly of the first member 32, so that the indicator 39 is partially observable. As illustrated in FIG. 5, in one example, when the magnitude of the external force is further increased, the indicator 39 is in the third state 136 and completely projects outwardly of the first member 32, so that the indicator 39 is fully observable. Moreover, when the indicator 39 is in the third state 136, a portion 152 of the plunger 60 may be observable to indicate that the external force 128 applied to the second member 36 is excessive.

As illustrated in FIG. 7, in one example, the indicator 39 is positioned on a surface 156 of the first-member projection 92. As illustrated in FIG. 6, in one example, when the magnitude of the external force 128 is below a specific threshold, the indicator 39 is in the first state 124 and the arm projection 88 engages the surface 156 of the first member projection 92 and covers the indicator 39, so that it is not observable. As illustrated in FIG. 8, in one example, when the magnitude of the external force 128 is increased to a specific range, the indicator 39 is in the second state 132 and the arm projection 88 is partially spaced away from the first member projection 92, so that the indicator 39 is partially observable. As illustrated in FIG. 9, in one example, when the magnitude of the external force is further increased, the indicator 39 is in the third state 136 and the arm projection 88 is further spaced away from the first member projection 92, so that the indicator 39 is fully observable. Moreover, when the indicator 39 in the third state 136, a portion 160 of the surface 156 on the first-member projection 92 below the indicator 39 may be observable to indicate that the external force 128 applied to the second member 36 is excessive.

In one aspect of the disclosure, which may include at least a portion of the subject matter of any of the preceding and/or following examples and aspects, the indicator 39 has a first auditory characteristic 164 in the first state 124, a second auditory characteristic 168 in the second state 132, and a third auditory characteristic 172 in the third state 136. The first auditory characteristic 164, the second auditory characteristic 168, and the third auditory characteristic are different. The first auditory characteristic 164, the second auditory characteristic 168, and the third auditory characteristic 172 may be provided using, e.g., an electromechanical device, such as an audio speaker (not shown). The apparatus 20 is capable of including a variety of additional or alternative perceivable characteristics to indicate to the user the amount of the biasing force 98 applied to the seal 24. For example, in addition to observable and audible characteristics, the perceivable characteristics may include, but are not limited to, tactile characteristics or other characteristics.

Referring primarily to FIG. 10, one example of the present disclosure relates to a method 200 of testing adhesion of the seal 24 to the surface 28 (operation 204). The method 200 includes applying a force (such as a biasing force 98) to the seal 24 and indicating an amount of the force applied to the seal 24 (operation 204).

The disclosure and drawing figure(s) describing the operations of the method(s) set forth herein should not be interpreted as necessarily determining a sequence of such operations. Rather, although one illustrative order is indicated, it is to be understood that the sequence of the operations may be modified when appropriate. Accordingly, certain operations may be performed in a different order or simultaneously. Additionally, in some aspects of the disclosure, not all operations described herein need be performed.

In one aspect of the disclosure, which may include at least a portion of the subject matter of any of the preceding and/or following examples and aspects, the method 200 includes using the indicator 39 to indicate the amount of the force applied to the seal 24 (see, e.g., FIGS. 2,4, 5, 6, 8, and 9) (operation 212).

In one aspect of the disclosure, which may include at least a portion of the subject matter of any of the preceding and/or following examples and aspects, the force is applied to the seal 24 using the seal-contact member 38 (see, e.g., FIGS. 4, 5, 8, and 9) (operation 216).

In one aspect of the disclosure, which may include at least a portion of the subject matter of any of the preceding and/or following examples and aspects, the method 200 also includes moving the seal-contact member 38 substantially parallel to the surface 28 while urging the seal-contact member 38 against the seal 24 with the force, such as the biasing force 98, in a direction substantially perpendicular to the surface 28 (see, e.g., FIGS. 4, 5, 8, and 9) (operation 220). In one example of use, an operator will grasp the apparatus 20, urge the apparatus 20 toward the seal 24, thereby urging the seal contact member 38 against the seal 24 with the biasing force 98, and move the apparatus substantially parallel to the surface 28. Movement of the apparatus 20 in this manner will move the seal contact member 38 substantially parallel to the surface 28 and apply a friction force to the seal 24, which results in peal stress applied to the seal 24.

In one aspect of the disclosure, which may include at least a portion of the subject matter of any of the preceding and/or following examples and aspects, the method 200 also includes evaluating an effect of applying the force to the seal 24 on the adhesion of the seal 24 to the surface 28 (operation 224), such as by viewing the indicator 39 and identifying the indicator's position or state (see, e.g., FIGS. 4, 5, 8, and 9). The effect may be different depending on the quality of the adhesion of the seal 24 to the surface 28. If the quality of the adhesion is poor or unacceptable, the effect may be a damaged seal. If the quality of the adhesion is good or acceptable, the effect may be no noticeable damage to the seal 24 or an acceptable amount of damage to the seal 24.

In one aspect of the disclosure, which may include at least a portion of the subject matter of any of the preceding and/or following examples and aspects, the method 200 also includes evaluating the effect on the adhesion of the seal 24 to the surface 28 after applying the force, such as the biasing force 98, to a single location of the seal 24 a plurality of times (operation 228). The number of times the biasing force is applied to a single location of the seal 24 may be dictated, e.g., by the type of sealant used to form the seal 24.

In one aspect of the disclosure, which may include at least a portion of the subject matter of any of the preceding and/or following examples and aspects, the method 200 also includes causing the indicator 39 to be in the first state 124 when the force applied to the seal 24 is in the first range (see, e.g., FIGS. 2 and 6) and causing the indicator 39 to be in the second state 132 when the force applied to the seal 24 is in the second range (see, e.g., FIGS. 4 and 8) (operation 232) that exceeds the first range (operation 232). The method 200 also includes causing the indicator 39 to be in the third state 136 when the force applied to the seal 24 is in the third range (see, e.g., FIGS. 5 and 9) (operation 232) that exceeds the second range (operation 232).

In one aspect of the disclosure, which may include at least a portion of the subject matter of any of the preceding and/or following examples and aspects, causing the indicator 39 to be in the first state 124 includes causing the indicator 39 to have the first visual characteristic 140 (see, e.g., FIGS. 2 and 6), causing the indicator 39 to be in the second state 132 includes causing the indicator 39 to have the second visual characteristic 144 (see, e.g., FIGS. 4 and 8), and causing the indicator 39 to be in the third state 136 includes causing the indicator 39 to have the third visual characteristic 148 (see, e.g., FIGS. 5 and 9) (operation 236). The first visual characteristic 140, the second visual characteristic 144, and the third visual characteristic 148 are different (operation 236).

In one aspect of the disclosure, which may include at least a portion of the subject matter of any of the preceding and/or following examples and aspects, causing the indicator 39 to have the first visual characteristic 140 includes concealing the indicator 39 (see, e.g., FIGS. 2 and 6), causing the indicator 39 to have the second visual characteristic 144 includes partially exposing the indicator 39 (see, e.g., FIGS. 4 and 8), and causing the indicator 39 to have the third visual characteristic 148 includes fully exposing the indicator 39 (see, e.g., FIGS. 5 and 9) (operation 240).

In one aspect of the disclosure, which may include at least a portion of the subject matter of any of the preceding and/or following examples and aspects, causing the indicator 39 to be in the first state 124 includes causing the indicator 39 to have the first auditory characteristic 164, causing the indicator 39 to be in the second state 132 includes causing the indicator 39 to have the second auditory characteristic 168, and causing the indicator 39 to be in the third state 136 includes causing the indicator 39 to have the third auditory characteristic 172 (operation 244). The first auditory characteristic 164, the second auditory characteristic 168, and the third auditory characteristic 172 are different (operation 244). As explained above, the first auditory characteristic 164, the second auditory characteristic 168, and the third auditory characteristic 172 may be provided using, e.g., an electromechanical device, such as an audio speaker (not shown).

Examples of the disclosure may be described in the context of an aircraft manufacturing and service method 1100 as shown in FIG. 11 and an aircraft 1102 as shown in FIG. 12. During pre-production, illustrative method 1100 may include specification and design 1104 of the aircraft 1102 and material procurement 1106. During production, component and subassembly manufacturing 1108 and system integration 1110 of the aircraft 1102 take place. Thereafter, the aircraft 1102 may go through certification and delivery 1112 to be placed in service 1114. While in service by a customer, the aircraft 1102 is scheduled for routine maintenance and service 1116 (which may also include modification, reconfiguration, refurbishment, etc.).

Each of the processes of the illustrative method 1100 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 12, the aircraft 1102 produced by the illustrative method 1100 may include an airframe 1118 with a plurality of high-level systems 1120 and an interior 1122. Examples of high-level systems 1120 include one or more of a propulsion system 1124, an electrical system 1126, a hydraulic system 1128, and an environmental system 1130. Any number of other systems may be included. Although an aerospace example is shown, the principles of the disclosure may be applied to other industries, such as the automotive and ship-building industries, among others.

Apparatus and methods shown or described herein may be employed during any one or more of the stages of the manufacturing and service method 1100. For example, components or subassemblies corresponding to component and subassembly manufacturing 1108 may be fabricated or manufactured in a manner similar to components or subassemblies produced while the aircraft 1102 is in service. Also, one or more aspects of the apparatus, method, or combination thereof may be utilized during the production states 1108 and 1110, for example, by substantially expediting assembly of or reducing the cost of an aircraft 1102. Similarly, one or more aspects of the apparatus or method realizations, or a combination thereof, may be utilized, for example and without limitation, while the aircraft 1102 is in service, e.g., maintenance and service 1116.

Different examples and aspects of the apparatus and methods are disclosed herein that include a variety of components, features, and functionality. It should be understood that the various examples and aspects of the apparatus and methods disclosed herein may include any of the components, features, and functionality of any of the other examples and aspects of the apparatus and methods disclosed herein in any combination, and all of such possibilities are intended to be within the spirit and scope of the present disclosure.

Having the benefit of the teachings presented in the foregoing description and the associated drawings, many modifications of the disclosed subject matter will become apparent to one skilled in the art to which this disclosure pertains. Therefore, it is to be understood that the disclosure is not to be limited to the specific examples and aspects provided and that modifications thereof are intended to be within the scope of the appended claims. Moreover, although the foregoing disclosure and the associated drawings describe certain illustrative combinations of elements and/or functions, it should be appreciated that different combinations of elements and/or functions may be realized without departing from the scope of the appended claims.

What is claimed is:

1. An apparatus for testing adhesion of a seal to a surface, the apparatus comprising: a first member that comprises a first end, a second end, and a cavity therein, wherein the first end of the first member comprises a first aperture therethrough and in communication with the cavity, wherein the second end of the first member includes a second aperture therethrough and in communication with the cavity, wherein the cavity comprises a narrow cavity portion toward the first end and a wide cavity portion toward the second end with a lip between the narrow and wide cavity portions; a second member movable relative to the first member, wherein the second member comprises a plunger that comprises a wide portion, a narrow portion arranged toward the first end of the first member relative to the wide portion of the plunger, and an indicator portion arranged toward the second end of the first member relative to the wide portion of the plunger, wherein the wide portion is arranged in the wide cavity portion of the cavity in the first member, and wherein the second member further comprises a seal-contact member extending from the second member through the first aperture in the first member; means for biasing the first member and the second member relative to each other with a biasing force; and an indicator on the indicator portion of the plunger, wherein the indicator extends out of the second aperture in the second end of the first member when the second member is displaced relative to the first member as the seal-contact member of the second member is urged against at least one of the seal or the surface, wherein different extensions of the indicator out of the second aperture correspond to different states of the indicator, which represent different levels of friction between the seal-contact member of the second member and the at least one of the seal or the surface.

2. The apparatus of claim 1, wherein the lip in the cavity engages the wide portion of the plunger to limit displacement of the second member relative to the first member.

3. The apparatus of claim 2, wherein the second member is linearly movable relative to the first member.

4. The apparatus of claim 3, wherein:
the indicator is in a first state when an external force applied to the second member in a direction opposite to the biasing force is in a first force range;
the indicator is in a second state when the external force is in a second force range, wherein the second force range exceeds the first force range; and
the indicator is in a third state when the external force is in a third force range, wherein the third force range exceeds the second force range.

5. The apparatus of claim 4, wherein the indicator has a first visual characteristic in the first state, a second visual characteristic in the second state, and a third visual characteristic in the third state, and wherein the first visual characteristic, the second visual characteristic, and the third visual characteristic are different.

6. The apparatus of claim 5, wherein the indicator is not observable in the first state, is partially observable in the second state, and is fully observable in the third state.

7. The apparatus of claim 4, wherein the indicator has a first auditory characteristic in the first state, a second auditory characteristic in the second state, and a third auditory characteristic in the third state, and wherein the first auditory characteristic, the second auditory characteristic, and the third auditory characteristic are different.

8. The apparatus of claim 1, wherein the seal-contact member is an elastic member.

9. The apparatus of claim 1, wherein the first member includes a body portion and a cap portion, wherein first portion defines a first part of the cavity and the cap portion defines a second part of the cavity, wherein internal threads in the body portion includes threadingly engage external threads on the cap portion, and wherein the second aperture is disposed through the cap.

10. The apparatus of claim 9, wherein the seal-contact member includes a nose portion and a coupling portion opposite the nose portion; and
further comprising a coupling member engaged with the first end of the second member, wherein the coupling member includes a cavity that engages the coupling portion of the seal contact member.

11. The apparatus of claim 1, wherein the seal-contact member includes a nose portion and a coupling portion opposite the nose portion; and
further comprising a coupling member engaged with the first end of the second member, wherein the coupling member includes a cavity that engages the coupling portion of the seal contact member.

12. A method of testing adhesion of a seal to a surface, the method comprising: applying a force to a first member of a testing apparatus, the testing apparatus including: the first member that comprises a first end, a second end, and a cavity therein, wherein the first end of the first member comprises a first aperture therethrough and in communication with the cavity, wherein the second end of the first member includes a second aperture therethrough and in communication with the cavity, wherein the cavity comprises a narrow cavity portion toward the first end and a wide cavity portion toward the second end with a lip between the narrow and wide cavity portions; a second member movable relative to the first member, wherein the second member comprises a plunger that comprises a wide portion, a narrow portion arranged toward the first end of the first member relative to the wide portion of the plunger, and an indicator portion arranged toward the second end of the first member relative to the wide portion of the plunger, wherein the wide portion is arranged in the wide cavity portion of the cavity in the first member, and wherein the second member further comprises a seal-contact member extending from the second member through the first aperture in the first member; means for biasing the first member and the second member relative to each other with a biasing force; and an indicator on the indicator portion of the plunger, wherein the indicator extends out of the second aperture in the second end of the first member when the second member is displaced relative to the first member as the seal-contact member of the second member is urged against at least one of the seal or the surface, wherein different extensions of the indicator out of the second aperture correspond to different states of the indicator, which represent different levels of friction between the seal-contact member of the second member and the at least one of the seal or the surface; wherein the force is transmitted to the second member via the means for biasing, and wherein the seal-contact member transmits the force to the seal; and indicating an amount of the force applied to the seal based on displacement of the second member relative to the first member.

13. The method of claim 12, further comprising: causing the indicator to be in a first state when the force applied to the seal is in a first range; causing the indicator to be in a second state when the force applied to the seal is in a second range, wherein the second range exceeds the first range; and causing the indicator to be in a third state when the force applied to the seal is in a third range, wherein the third range exceeds the second range.

14. The method of claim 13, wherein:
causing the indicator to be in the first state comprises causing the indicator to have a first visual characteristic;
causing the indicator to be in the second state comprises causing the indicator to have a second visual characteristic; and
causing the indicator to be in the third state comprises causing the indicator to have a third visual characteristic, and wherein the first visual characteristic, the second visual characteristic, and the third visual characteristic are different.

15. The method of claim 14, wherein:
causing the indicator to have the first visual characteristic comprises concealing the indicator;
causing the indicator to have the second visual characteristic comprises partially exposing the indicator; and
causing the indicator to have the third visual characteristic comprises fully exposing the indicator.

16. The method of claim 13, wherein:
causing the indicator to be in the first state comprises causing the indicator to have a first auditory characteristic;
causing the indicator to be in the second state comprises causing the indicator to have a second auditory characteristic; and
causing the indicator to be in the third state comprises causing the indicator to have a third auditory characteristic, and wherein the first auditory characteristic, the second auditory characteristic, and the third auditory characteristic are different.

17. The method of claim 12, further including moving the seal-contact member substantially parallel to the surface while urging the seal-contact member against the seal with the force in a direction substantially perpendicular to the surface.

18. The method of claim 12, further including evaluating an effect of applying the force to the seal on the adhesion of the seal to the surface.

19. The method of claim 18, further including evaluating the effect on the adhesion of the seal to the surface after applying the force to a single location of the seal a plurality of times.

20. An apparatus for testing adhesion of a seal to a surface, the apparatus comprising:
a first member that includes a first body with a first end and a second end arranged along a first direction, wherein the first body includes an aperture located between the proximal and distal ends and in a second direction transverse to the first direction, wherein the first body further includes a first projection extending away from the body adjacent to the aperture in the second direction, and wherein the first projection includes a surface facing the second direction;
a second member that includes a second body arranged along the first direction and pivotably connected via a pin to the first member, wherein the second body includes a second projection extending from the second body through the aperture in the first body and adjacent to the surface of the first projection, wherein a proximal end of the second member includes a seal-contact member extending from the second body in a direction opposite the second direction, and wherein the pin is arranged between the second projection and the seal-contact member;
means for biasing the first member and the second member with a biasing force; and
an indicator arranged on the surface of the first projection;
wherein different amounts of the indicator are covered by the second projection relative when the second member is displaced relative to the first member as the seal-contact member is urged against at least one of the seal or the surface, wherein different amounts of the indicator uncovered by the second projection correspond to different states, wherein the different states indicate different degrees of displacement of the second member relative to the first member, and wherein the different degrees of displacement of the second member relative to the first member correspond to different degrees of urging of the seal-contact member against the at least one of the seal or the surface.

\* \* \* \* \*